May 12, 1936. F. E. CREMER Plant Pat. 177
ROSE
Filed Dec. 21, 1935
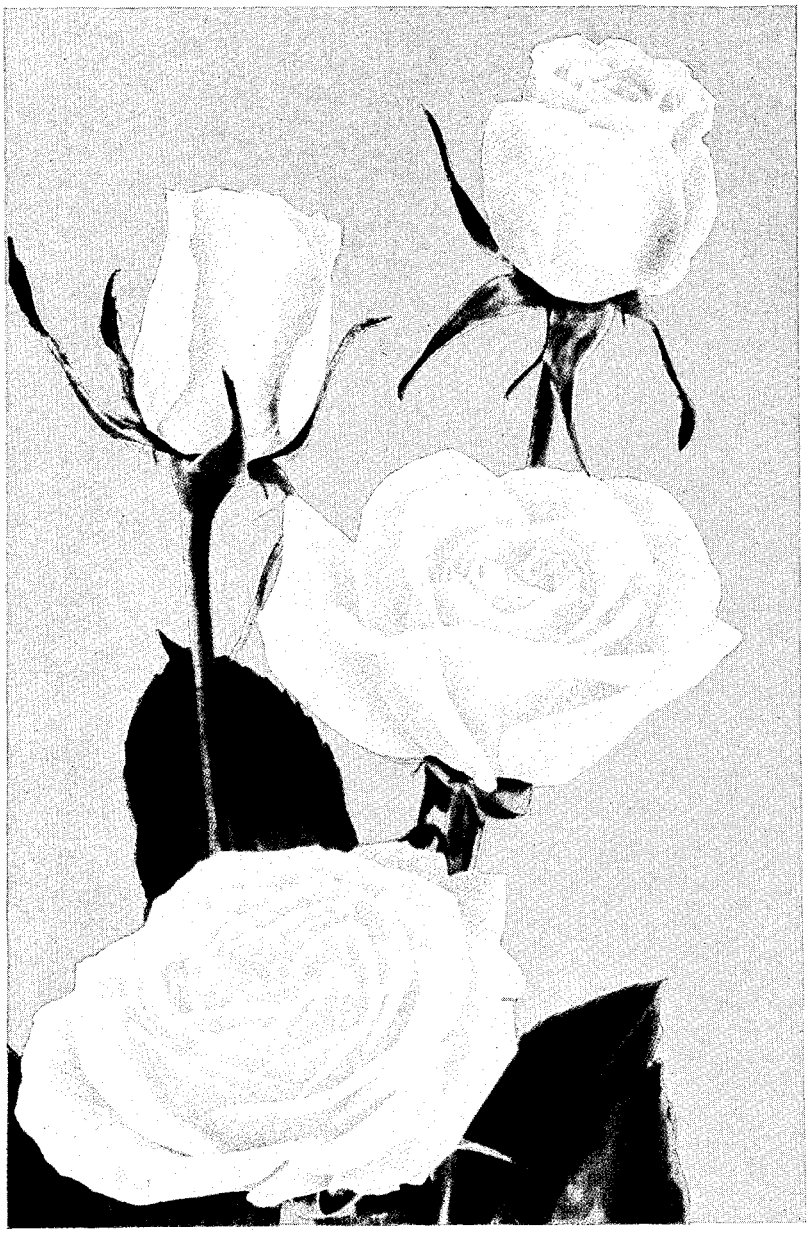
Inventor
Frank Eugene Cremer
By Orville M. Kile
Plant Patent Agent Patented May 12, 1936

Plant Pat. 177

UNITED STATES PATENT OFFICE

177

ROSE

Frank Eugene Cremer, Hanover, Pa.

Application December 21, 1935, Serial No. 55,645

1 Claim. (Cl. 47—61)

My present invention relates to a new and improved variety of hybrid tea rose plant, involving novel and interesting color effects and other desirable qualities.

This new variety is a sport of Souvenir. I have reproduced it through three generations and have demonstrated that its qualities are fixed.

The accompanying illustrations, in the original, show in full color and approximately full size, two opening buds and two flowers in more mature stages, together with foliage and stems—all depicted as nearly as possible in their true forms and colors.

The following is a detailed description of this new variety.

*The bush*

*Growth.*—In growth habits this variety somewhat resembles Talisman, but the flower stems are stronger and the necks straighter.

It is a very vigorous grower, a free bloomer, and is apparently disease resistant.

*Foliage.*—The leaf branches are extraordinarily plentiful below the long glossy light green peduncle. The joints are exceptionally short. Six to 10 inches below the flower the leaf branches are often only 1¼ to 1½ inches apart and the usual spacing on the variety is but 1½ to 2½ inches.

The five leaflets are of medium size 2½ to 3 inches long and rather narrow for their length. Their petioles are extraordinarily short. The leaves are smooth on the upper surface and only slightly waved at the edges, having small regular serrations rather few in number. Veins are not prominent. The leaves are somewhat lighter than "Forest green" in color (Plate XVII, Ridgway's Color Standards and Nomenclature).

*Stems* are rather straight, particularly the peduncles, and medium in thickness. The peduncles are 7 to 9 inches long and of a beautiful glossy light green approximately "Apple green" (Plate XVII).

*Stipules* are wide and have long pointed tips.

*Sepals.*—Medium length and not inclined to foliaceous form.

*Thorns.*—Below the peduncle white to pinkish thorns are found, rather large, numerous, 3 or 4 between joints, straight rather than hooked and placed at a downward-pointing angle.

*Hips* are heavy and wide and inclined to be abrupt rather than tapering; this is perhaps a source of nourishment after flowers are cut.

*The flowers*

*Buds* are inclined to be cup shaped rather than the true urn shape. The bud shows darker shades of color than the opened flower.

The cut bud opens slowly and the flower retains its petals until they are completely dried out. Even on cut flowers the petals will not shatter and drop off.

The usual length of time required for a tight cut bud to open into full flower is 6 days—in 2 days the bud opens sufficiently for a good show of color but 4 days are required before the blossom is well opened and another day or two before fully opened. After becoming fully opened, at least 3 days elapse before it begins to show signs of drying out. In other words, a period of at least 9 days elapses between the tight bud stage and the drying stage. Even then the petals do not fall. These observations were taken in December and apply to greenhouse-grown flowers subjected to usual room temperatures and reasonable care.

*Flowers.*—This variety produces large full-petaled, substantial flowers. The width of the open flower averages about 4 inches. At the beginning of December and in the latitude of central Pennsylvania the number of petals per flower is 45 to 50. Only a few of these petals are rudimentary, mostly being large and well rounded in shape.

*Colors.*—The colors of the flowers change materially with changes in degree of maturity.

When the flower is in its prime the dominant color tone is "Salmon-orange" (Plate II, Ridgway's). When the one-half to three-fourths opened flower is viewed from the side so as to show the outer surface of the petals there is a distinct suffusion of pink. As the blossoms age the salmon-orange color fades somewhat but the outer petals, being recurved, present a view of the inner surfaces which is a considerably deeper shade of pink. Thus the flower in maturity shows a deeper pink on its outer circumference than is the case when the flower is only one-half to two-thirds open.

The opening bud shows darker shades of pink than at any other stage, being between "Jasper red" (Plate XIII) and "Grenadine red" (Plate II).

Each petal of the opened flower has a "Light cadmium" (Plate IV) basal area, being brighter and confined to a smaller area on the outside surface and fainter and more diffused on the inner surface. The petals are not notably veined.

*Pistils and Stamens* are moderately plentiful making a bulky mass near the point of attachment and contributing toward making a full centered flower. The stamens are notably longer than the pistils, red in color and mounted by buff colored anthers of relatively small size. The pistils are of moderate number, greenish white except for the top quarter of each filament which is reddish except at extreme top end which is a waxy white. Considerable pithy matter around the ovaries and among the pistils and stamens adds to the bulk and helps account for the large hips.

*Fragrance.*—Moderately fragrant.

Having thus disclosed my invention, I claim;

The new variety of rose plant herein shown and described, characterized particularly by its vigorous growth and free blooming habits, its profuse foliage and its full-petaled, substantial flowers of distinctive salmon-orange color changing as described and having long-lasting, non-shattering qualities.

FRANK EUGENE CREMER.